United States Patent
Parker

(10) Patent No.: US 8,992,591 B2
(45) Date of Patent: Mar. 31, 2015

(54) DELIVERY SYSTEM WITH LOW LONGITUDINAL COMPRESSIBILITY

(75) Inventor: Fred T. Parker, Unionville, IN (US)

(73) Assignee: Cook Medical Technologies LLC, Bloomington, IN (US)

( * ) Notice: Subject to any disclaimer, the term of this patent is extended or adjusted under 35 U.S.C. 154(b) by 1731 days.

(21) Appl. No.: 12/435,689

(22) Filed: May 5, 2009

(65) Prior Publication Data

US 2009/0281610 A1    Nov. 12, 2009

Related U.S. Application Data

(60) Provisional application No. 61/051,177, filed on May 7, 2008.

(51) Int. Cl.
*A61F 2/06* (2013.01)
*A61F 2/966* (2013.01)
*A61F 2/95* (2013.01)

(52) U.S. Cl.
CPC . *A61F 2/966* (2013.01); *A61F 2/95* (2013.01); *A61F 2002/9522* (2013.01)
USPC ........ 623/1.11; 623/1.12; 623/1.23; 606/108; 604/103.09; 604/508; 604/510

(58) Field of Classification Search
USPC ...................... 623/1.11, 1.12, 1.23; 606/108; 604/103.9, 508, 510
See application file for complete search history.

(56) References Cited

U.S. PATENT DOCUMENTS

| | | | |
|---|---|---|---|
| 4,665,918 A | 5/1987 | Garza et al. | 128/343 |
| 5,380,304 A | 1/1995 | Parker | 604/282 |
| 5,397,345 A | 3/1995 | Lazarus | 623/1 |
| 5,772,669 A | 6/1998 | Vrba | 606/108 |
| 5,817,101 A | 10/1998 | Fiedler | 606/108 |
| 6,113,608 A | 9/2000 | Monroe et al. | 606/108 |
| 6,117,140 A | 9/2000 | Munsinger | 606/108 |
| 6,939,337 B2 | 9/2005 | Parker et al. | 604/523 |
| 7,163,552 B2 * | 1/2007 | Diaz | 623/1.12 |
| 2001/0034514 A1 | 10/2001 | Parker | 604/523 |
| 2006/0015168 A1 | 1/2006 | Gunderson | 623/1.11 |
| 2007/0208405 A1 * | 9/2007 | Goodin et al. | 623/1.11 |
| 2007/0233224 A1 | 10/2007 | Leynov et al. | 623/1.11 |

* cited by examiner

*Primary Examiner* — Victor Nguyen
*Assistant Examiner* — Kevin Everage
(74) *Attorney, Agent, or Firm* — Brinks Gilson & Lione

(57) ABSTRACT

An improved delivery system for an implantable medical device includes a retention sheath having a proximal end, a distal end, and an inner lumen extending from the proximal end to the distal end. The implantable medical device is disposed within the inner lumen of the retention sheath, which restrains the implantable medical device. A plurality of substantially incompressible rings are disposed within the inner lumen of the retention sheath in a stacked co-axial configuration that extends from the proximal end of the retention sheath in a pre-deployment position to a proximal end of the implantable medical device. Each ring in the plurality of separate rings abuts at least a portion of an adjacent ring. The plurality of separate rings is configured to prevent the implantable medical device from moving toward a proximal end of the retention sheath when the retention sheath is moved from the pre-deployment position to a deployment position.

20 Claims, 11 Drawing Sheets

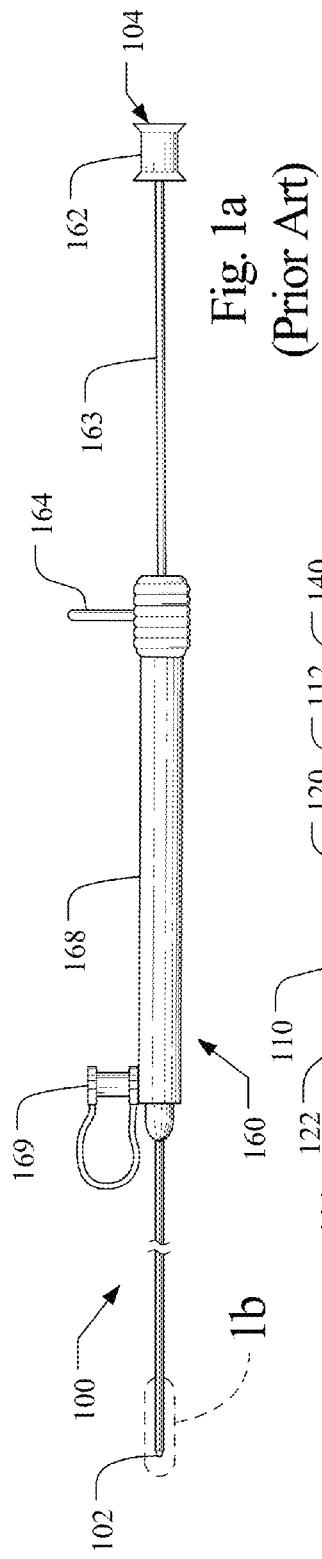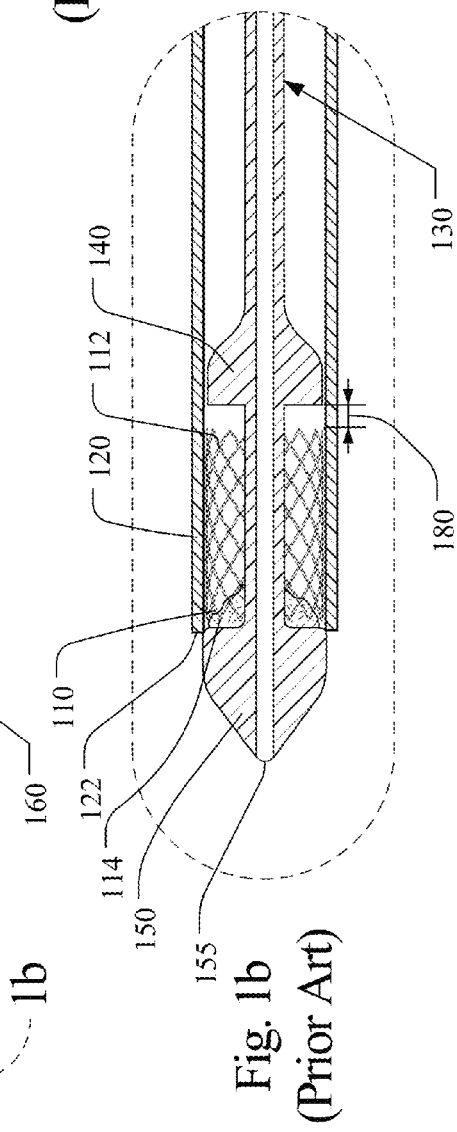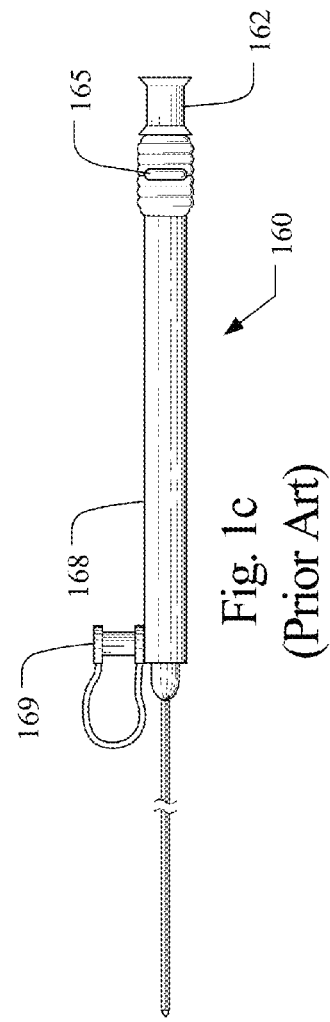

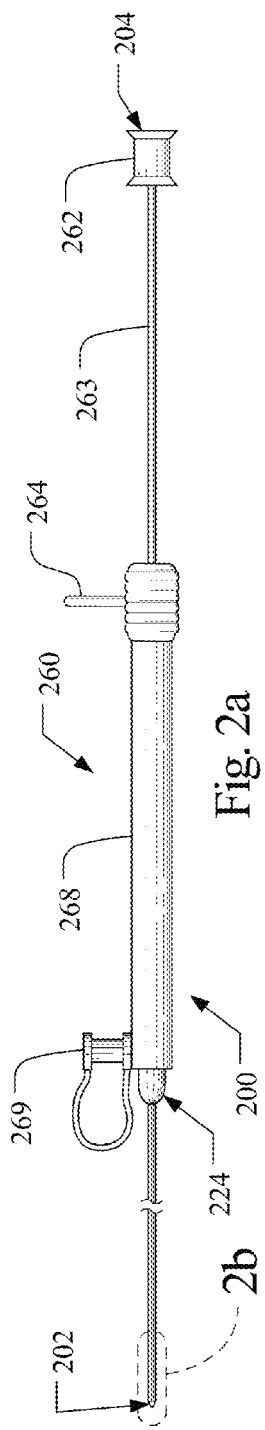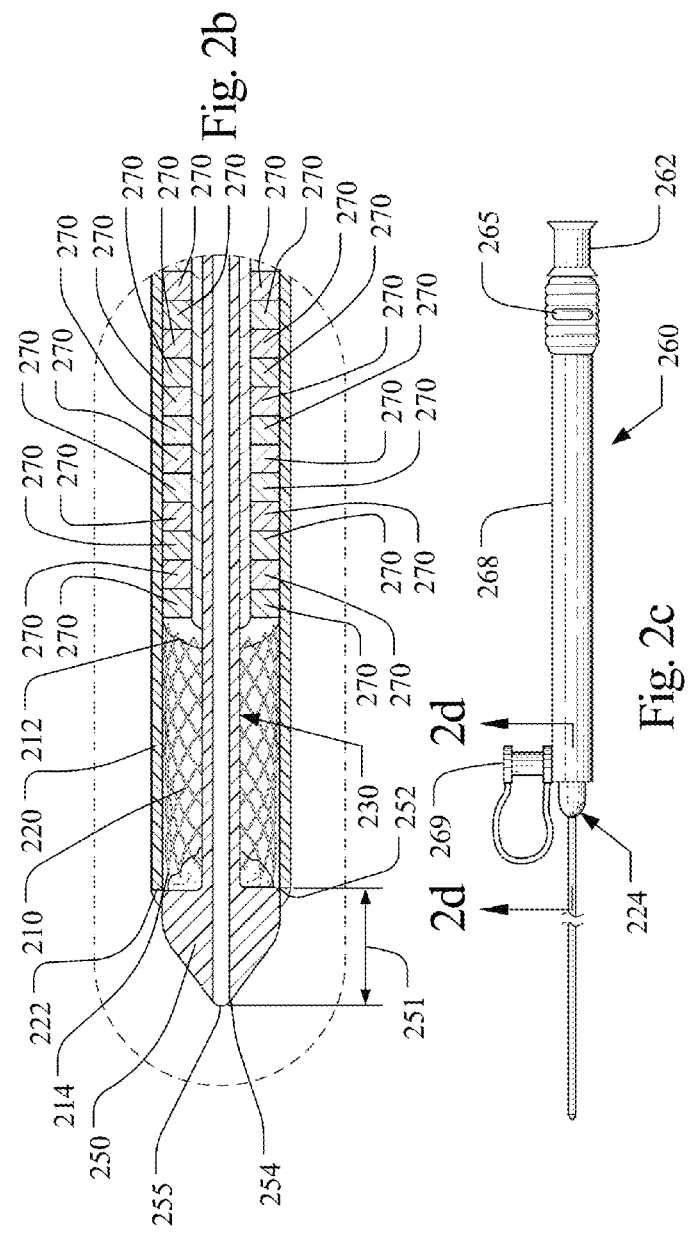

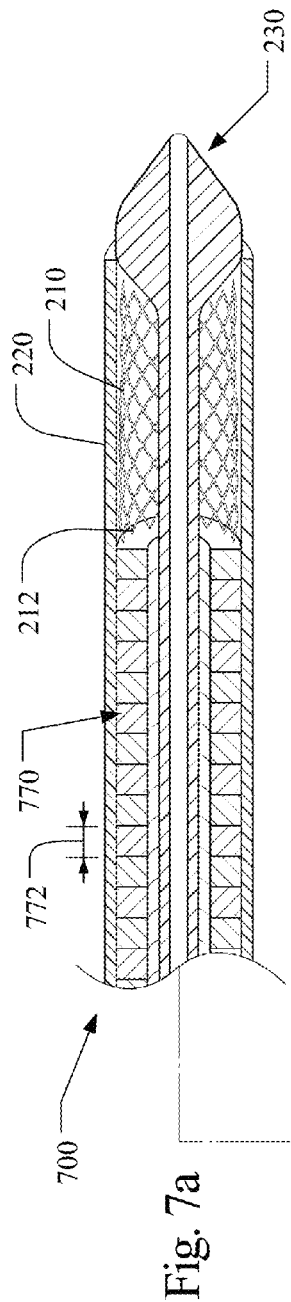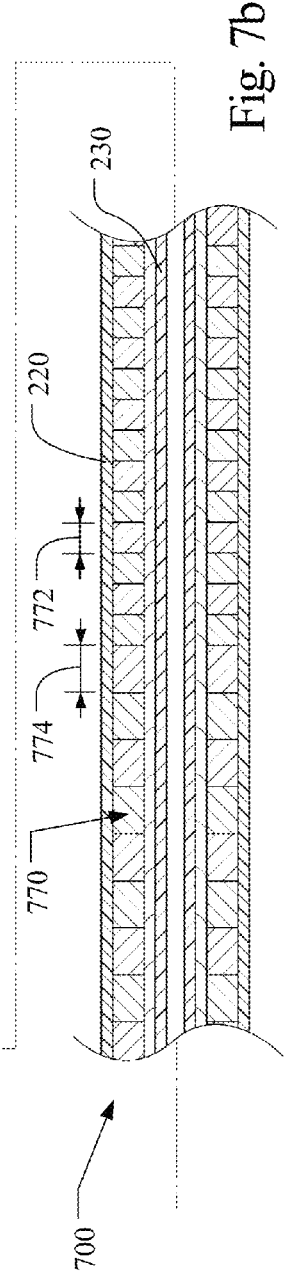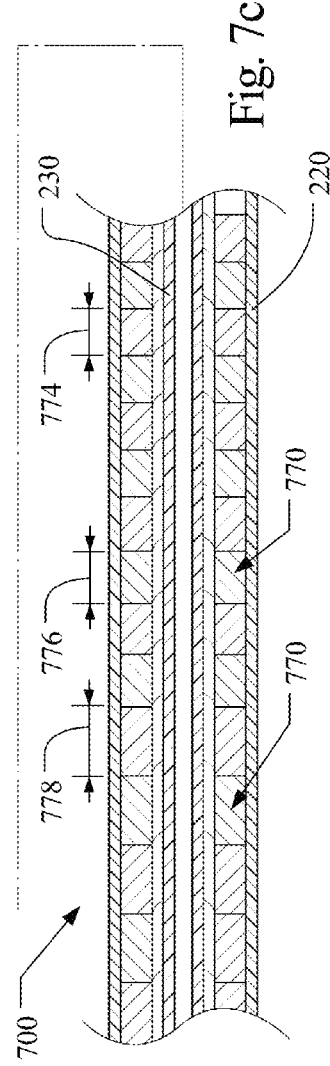

DELIVERY SYSTEM WITH LOW LONGITUDINAL COMPRESSIBILITY

RELATED APPLICATION

The present application claims the benefit of U.S. Provisional Application No. 61/051,177, filed on May 7, 2008, the entirety of which is hereby incorporated by reference.

BACKGROUND

1. Field of the Invention

The present invention relates generally to medical devices and more particularly to delivery systems for implantable medical devices, such as self-expanding stents.

2. Technical Background

Stents have become a common alternative for treating vascular conditions because stenting procedures are considerably less invasive than other alternatives. As an example, stenoses in the coronary arteries have traditionally been treated with bypass surgery. In general, bypass surgery involves splitting the chest bone to open the chest cavity and grafting a replacement vessel onto the heart to bypass the stenosed artery. However, coronary bypass surgery is a very invasive procedure that presents increased risk and requires a long recovery time for the patient. By contrast, stenting procedures are performed transluminally and do not require open surgery. Thus, recovery time is reduced and the risks of surgery are minimized.

Many different types of stents and stenting procedures are possible. In general, however, stents are typically designed as tubular support structures that may be inserted percutaneously and transluminally through a body passageway. Typically, stents are adapted to be compressed and expanded between a smaller and larger diameter. However, other types of stents are designed to have a fixed diameter and are not generally compressible. Although stents may be made from many types of materials, including non-metallic materials and natural tissues, common examples of metallic materials that may be used to make stents include stainless steel and Nitinol. Other materials may also be used, such as cobalt-chrome alloys, amorphous metals, tantalum, platinum, gold, titanium, polymers and/or compatible tissues. Typically, stents are implanted within an artery or other passageway by positioning the stent within the lumen to be treated and then expanding the stent from a compressed diameter to an expanded diameter. The ability of the stent to expand from a compressed diameter makes it possible to thread the stent through narrow, tortuous passageways to the area to be treated while the stent is in a relatively small, compressed diameter. Once the stent has been positioned and expanded at the area to be treated, the tubular support structure of the stent contacts and radially supports the inner wall of the passageway. The implanted stent may be used to mechanically prevent the passageway from closing in order to keep the passageway open to facilitate fluid flow therethrough.

Stents may also be used in combination with other components to treat a number of medical conditions. For example, stent-graft assemblies are commonly used in the treatment of aneurysms. As those in the art well know, an aneurysm is an abnormal widening or ballooning of a portion of an artery. Generally, this condition is caused by a weakness in the blood vessel wall. High blood pressure and atherosclerotic disease may also contribute to the formation of aneurysms. Common types of aneurysms include aortic aneurysms, cerebral aneurysms, popliteal artery aneurysms, mesenteric artery aneurysms, and splenic artery aneurysms. However, it is also possible for aneurysms to form in blood vessels throughout the vasculature. If not treated, an aneurysm may eventually rupture, resulting in internal hemorrhaging. In many cases, the internal bleeding may be so massive that a patient can die within minutes of an aneurysm rupture. For example, in the case of aortic aneurysms, the survival rate after a rupture can be as low as 20%.

Traditionally, aneurysms have been treated with surgery. For example, in the case of an abdominal aortic aneurysm, the abdomen is surgically opened, and the widened section of the aorta is typically dissected longitudinally. A graft material, such as Dacron, is then inserted into the vessel and sutured at each end to the inner wall of the non-widened portions of the vessel. The dissected edges of the vessel may then be overlapped and sutured to enclose the graft material within the vessel. In smaller vessels where the aneurysm forms a balloon-like bulge with a narrow neck connecting the aneurysm to the vessel, the surgeon may put a clip on the blood vessel wall at the neck of the aneurysm between the aneurysm and the primary passageway of the vessel. The clip then prevents blood flowing through the vessel from entering the aneurysm.

An alternative to traditional surgery is endovascular treatment of the blood vessel with a stent-graft. This alternative involves implanting a stent-graft in the blood vessel across the aneurysm using conventional catheter-based placement techniques. The stent-graft treats the aneurysm by sealing the wall of the blood vessel with a generally impermeable graft material. Thus, the aneurysm is sealed off and blood flow is kept within the primary passageway of the blood vessel. Increasingly, treatments using stent-grafts are becoming preferred since the procedure results in less trauma and faster recuperation.

Self-expanding stents are one common type of stent used in medical procedures. Self-expanding stents are increasingly being used by physicians because of their adaptability to a variety of different conditions and procedures. Self-expanding stents are usually made of shape memory materials or other elastic materials that act like a spring. Typical metals used in this type of stent include Nitinol and stainless steel. However, other materials may also be used. To facilitate stent implantation, self-expanding stents are normally installed on the end of a catheter in a low profile, compressed state. The stent is typically inserted into a sheath at the end of the catheter, which restrains the stent in the compressed state. The stent and catheter assembly is then guided to the portion of the vessel to be treated. Once the catheter and stent are positioned adjacent the portion to be treated, the stent is released by pulling, or withdrawing, the sheath rearward. Normally, a stop or other feature is provided on the catheter to prevent the stent from moving rearward with the sheath. After the stent is released from the retaining sheath, the stent springs radially outward to an expanded diameter until the stent contacts and presses against the vessel wall. Traditionally, self-expanding stents have been used in a number of peripheral arteries in the vascular system due to the elastic characteristic of these stents. One advantage of self-expanding stents for peripheral arteries is that traumas from external sources do not permanently deform the stent. As a result, the stent may temporarily deform during unusually harsh traumas and spring back to its expanded state once the trauma is relieved. However, self-expanding stents may be used in many other applications as well.

The above-described examples are only some of the applications in which stents are used by physicians. Many other applications for stents are known and/or may be developed in the future.

SUMMARY

Delivery systems are described which may allow for more precise placement of implantable medical devices. The delivery systems include a retention sheath that houses and restrains the implantable medical device, and a plurality of separate abutting rings disposed within the retention sheath in a stacked co-axial configuration. The plurality of separate rings may extend from a proximal end of the retention sheath to a proximal end of the implantable medical device. When the retention sheath is moved from a pre-deployment position to a deployment position, the proximal end of the implantable medical device contacts a ring in the plurality of rings located closest to the proximal end of the implantable medical device, and the plurality of separate abutting rings prevents the implantable medical device from moving axially toward the proximal end of the retention sheath. Additional details and advantages are described below in the detailed description.

The invention may include any of the following aspects in various combinations and may also include any other aspect described below in the written description or in the attached drawings.

In one aspect, a delivery system for an implantable medical device includes a retention sheath comprising a proximal end, a distal end, and an inner lumen extending from the proximal end to the distal end. The retention sheath is movable in an axial direction from a pre-deployment position to a deployment position. The implantable medical device, for example, a self-expanding stent, is disposed within the inner lumen of the retention sheath, and the retention sheath restrains the implantable medical device. A plurality of separate rings are disposed within the inner lumen of the retention sheath in a stacked co-axial configuration. The plurality of separate rings may extend from the proximal end of the retention sheath in the pre-deployment position to a proximal end of the implantable medical device. Preferably, each of the rings abuts at least a portion of an adjacent ring. The plurality of separate rings is preferably configured to prevent the implantable medical device from moving toward a proximal end of the retention sheath when the retention sheath is moved from the pre-deployment position to the deployment position.

In another aspect, the delivery system also includes an inner catheter having an outer surface with a diameter that is less than an inner diameter of the plurality of separate rings. The inner catheter includes a distal tip having an outer diameter that is greater than the inner diameter of the plurality of separate rings. The inner catheter is disposed within a space defined by the inner diameter of the plurality of separate rings.

In another aspect, each ring in the plurality of separate rings abuts at least a portion of an adjacent ring, and the plurality of separate rings is configured to prevent the implantable medical device from moving toward a proximal end of the retention sheath when the retention sheath is moved from the pre-deployment position to the deployment position. Each of the rings also has a thickness as measured in an axial direction, and the thickness may vary among the rings in the plurality of separate rings. The thickness of the individual rings of the plurality of separate rings may increase in an axial direction toward the proximal end of the retention sheath.

The individual rings in the plurality of the separate rings may have various cross-sectional shapes and may be made of metal, for example and without limitation, nitinol, titanium or stainless steel. One or more of the rings may also be radiopaque.

A method of manufacturing a delivery system may include providing a retention sheath including an outer diameter and an inner lumen extending therethrough, the inner lumen forming an opening at the distal end of the retention sheath, and loading an implantable medical device, for example, a self-expanding stent, into the opening at the distal end of the retention sheath. An inner catheter may be inserted into the inner lumen of the retention sheath through the opening at the distal end of the retention sheath. A plurality of separate rings is placed around a mandrel, and the mandrel is inserted into a proximal end of a lumen of the inner catheter. The individual rings of the plurality of separate rings are moved from the mandrel into the inner lumen of the retention sheath by transferring the plurality of separate rings from the mandrel to an annular space formed between the outer surface of the inner catheter and the inner surface of the retention sheath. The plurality of separate rings may be transferred such that a distal most ring in the plurality of separate rings abuts a proximal end of the implantable medical device.

The foregoing paragraphs have been provided by way of general introduction, and are not intended to limit the scope of the following claims. The presently preferred embodiments, together with further advantages, will be best understood by reference to the following detailed description taken in conjunction with the accompanying drawings.

BRIEF DESCRIPTION OF THE DRAWINGS

The invention may be more fully understood by reading the following description in conjunction with the drawings, in which:

FIG. 1(a) is a side view of a conventional implantable self-expanding medical device delivery system in an undeployed state;

FIG. 1(b) is a side cross-sectional view of a distal tip portion of the conventional implantable self-expanding medical device delivery system of FIG. 1(a);

FIG. 1(c) is a partial side view of a control device for the conventional implantable self-expanding medical device delivery system of FIG. 1(a) in a deployed state;

FIG. 2(a) is a side view of an embodiment of an implantable self-expanding medical device delivery system according to the present invention;

FIG. 2(b) is a side cross-sectional view of a distal tip portion of the delivery system of FIG. 2(a);

FIG. 2(c) is a partial side view of a control device for the delivery system of FIG. 2(a) in a deployed state;

FIG. 7(a) is a partial side cross-sectional view of a distal tip of another embodiment of a delivery system according to the present invention;

FIG. 7(b) is a partial side cross-sectional view of an intermediate portion of the delivery system of FIG. 7(a); and FIG. 7(c) is a side cross-sectional view of a portion disposed near a proximal end of the delivery system of FIG. 7(a).

DETAILED DESCRIPTION

Figure 2D:
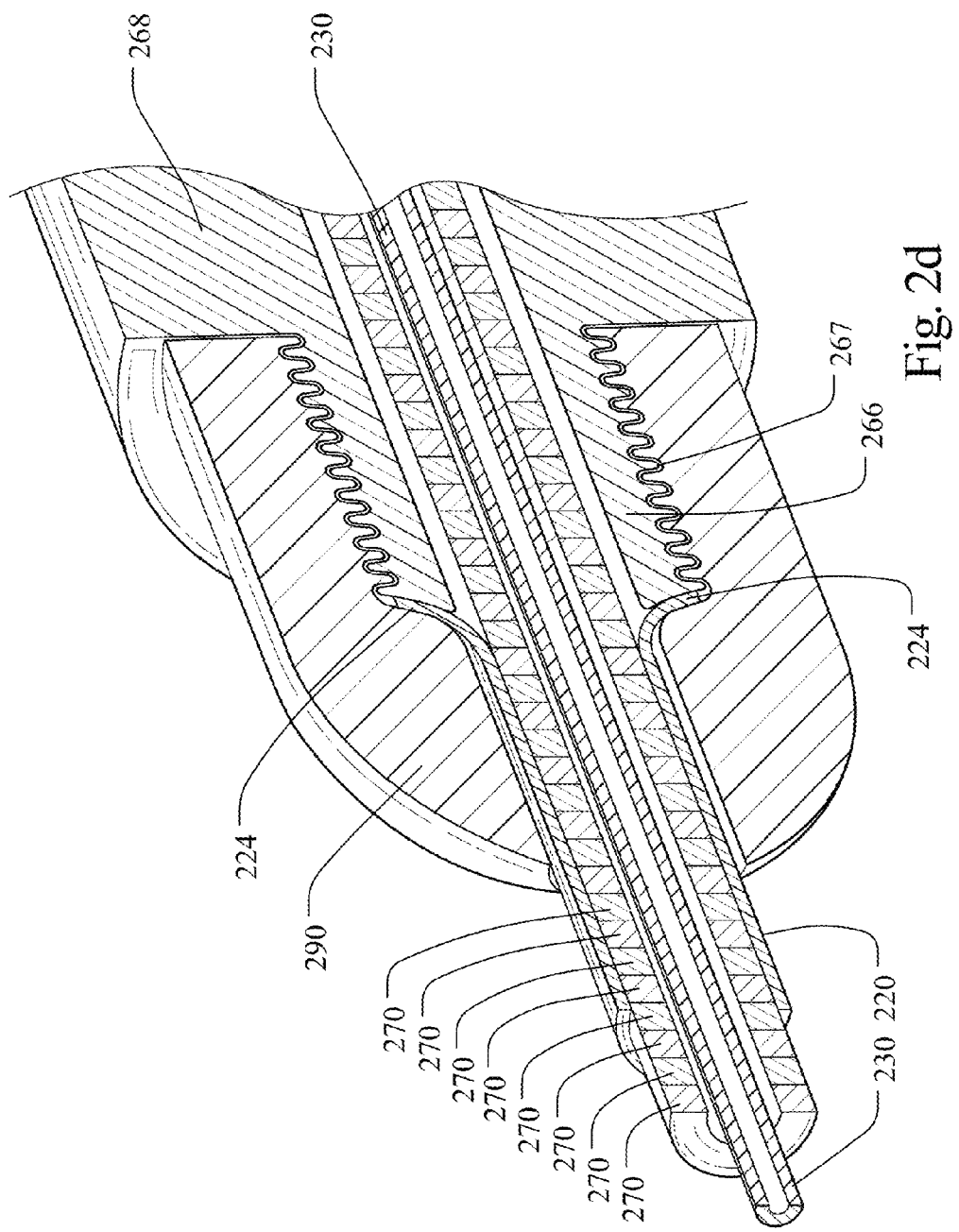
FIG. 2(d) is a close-up side cross-sectional view of the distal portion of the control device for the delivery system of FIG. 2(a)
Figure 2E:
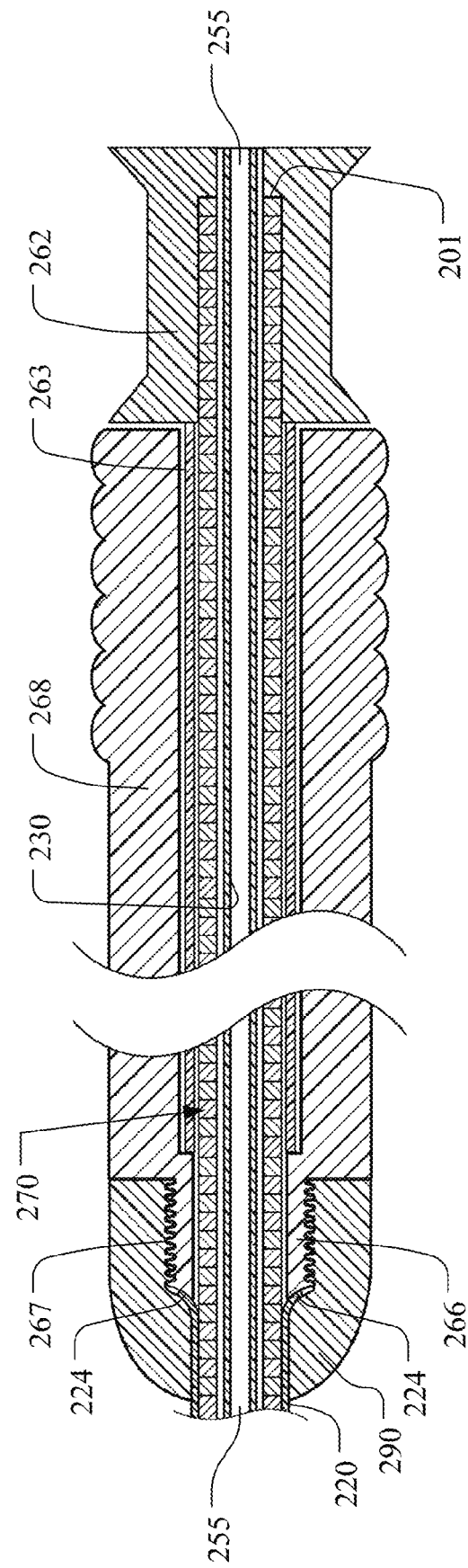
FIG. 2(e) is a side cross-sectional view of the control device for the delivery system of FIG. 2(a)

The term "axial" refers to the lengthwise direction 1 between the distal end 102 and the proximal end 104 of an implantable medical device delivery system 100. The axial direction is aligned with a central axis of the delivery system as shown in the Figures, and denoted as line x-x in FIG. 6(b). The term "distal" and variations thereof refer to the position or orientation relative to the distal end 102, 202 of an implantable medical device delivery system, which is configured to receive a guidewire and be inserted into a patient's vasculature, while the term "proximal" and variations thereof refer to the position or orientation relative to the proximal end 104, 204 of the delivery system 100, 200, as shown in FIGS. 1(a) and 2(a). The term implantable medical device refers to medical devices capable of being implanted within a human being including, for example and without limitation, self-expanding stents, balloon expanding stents, coils, filters, valves, baskets, and endovascular grafts used in the treatment of patients with abdominal aortic or aorto-iliac aneurisms. While the following description of the embodiments of the present invention will be made with regard to self-expanding stents, it should be understood that the present invention is not limited thereto. Moreover, the present invention is not limited to delivery systems for implantable medical devices, for example, and may be employed in any catheter requiring the exertion of significant axial force at the proximal end to produce a desired effect at the distal end, such as an occluding device.

Referring now to the figures, FIGS. 1(a)-1(c) show a conventional delivery system 100 for a self-expanding stent 110. The delivery system includes a retention sheath 120, a self-expanding stent 110, an inner catheter 130, and a control device 160.

As is well understood by those skilled in the art, the self-expanding stent 110 is initially mounted within the retention sheath 120 at the distal end of the inner catheter 130. Various designs known in the art may be used for the self-expanding stent 110. For example, the self-expanding stent 110 may be made with serpentine rings interconnected with longitudinal struts. The stent 110 may also be made from a braided framework of wire filaments. Other well-known stent structures are also possible. Various materials may be used for the self-expanding stent 110, such as nitinol or stainless steel.

Typically, the inner catheter 130 includes a stop 140 that extends radially outward from a guidewire lumen 155 of the inner catheter 130, and a distal tip 150 that may be bonded to the distal end of the inner catheter 130 using an adhesive or the like. A distal surface of the stop 140 is located adjacent the proximal end 112 of the stent 110.

The stent 110 may be released from the delivery system by withdrawing the retention sheath 120 proximally relative to the inner catheter 130. The self expanding stent 110 typically presses outward against the inner surface of the retention sheath 120, thereby producing a small amount of friction between the stent 110 and the retention sheath 120. However, the stop 140 prevents the stent 110 from moving proximally with the retention sheath 120 as the retention sheath 120 is withdrawn. In effect, the stent 110 is pushed out of the retention sheath 120 by the stop 140 as the retention sheath 120 is withdrawn.

In the case where the distal tip 150 is bonded to the inner catheter 130, an undesirable gap 180 may be introduced between a distal end of the stop 140 and the proximal end of the stent 112 to accommodate the bonding process. For example, the gap may be between 0.118 and 0.934 inches in length, as measured in the axial direction. When the retention sheath 120 is withdrawn, the stent 110 initially moves proximally with the retention sheath through the gap 180 until the proximal end of the stent 112 contacts the distal end of the stop 140. Once the proximal end of the stent 112 contacts the distal end of the stop 140, the stop 140 prevents the stent 110 from continuing to move proximally, thereby separating the stent 110 from the retention sheath 120. However, because the stent 110 initially moves proximally with the retention sheath 120 through the gap 180, a slight delay in deployment may occur. This delay in deployment may also cause inaccuracy in placement of the stent 110.

A control device 160, which may be used to deploy the stent 110, is shown in FIGS. 1(a) and 1(c). FIG. 1(a) shows the control device 160 in an initial configuration before the stent 110 is deployed. FIG. 1(c) shows the control device 160 in a final configuration after the stent 110 is deployed. Typically, the control device 160 is located outside of the patient's body and is operated by the physician to control the deployment of the stent 110 at a desired treatment site within the patient's body.

As shown in FIGS. 1(b) and (c), the control device 160 may include a proximal control knob 162. The control device 160 may also include a control handle 168 located distal from the control knob 162. The control knob 162 may be attached to a shaft 163 that extends through the control handle 168. The shaft 163 is attached to the inner catheter 130. The control handle 160 is attached to the retention sheath 120. If desired, a guidewire lumen 155 may pass through the shaft 163 and the control knob 162. Thus, a guidewire 2 (see FIGS. 3-4) may pass through the inner catheter 130, the control device 160, and out the proximal end of the control knob 162.

A port 169 may also be provided on the control handle 168 to pass fluids through the delivery system to the treatment site. Preferably, the port 169 is in communication with the annular space between the inner catheter 130 and the retention sheath 120. Thus, fluid may be supplied through the space between the inner catheter 130 and the retention sheath 120. Typically the fluid is supplied after the stent is deployed because it is difficult to move fluid past the compressed stent. The fluid may exit from the delivery system at the distal end of the retention sheath 120. For example, the port 169 may be useful in supplying contrast solution to the treatment site. Contrast solution is useful in angiography procedures to visualize an internal organ before, during or after deployment of the stent 110. Fluids, such as contrast fluid, may also be supplied through the guidewire lumen 155 before or after to deploying the stent.

A locking tab 164 may also be provided. The locking tab 164 is installed in a slot 165 in the control handle 168 when the control device 160 is in the initial configuration before the stent 110 is released. The locking tab 164 locks the control handle 168 to the shaft 163 to prevent relative movement between the control handle 168 and the control knob 162. Thus, the locking tab 164 prevents premature deployment or partial deployment of the stent 110.

In order to deploy the stent 110, the locking tab 164 is removed from the control handle 168. This unlocks the control device 160 so that the control handle 168 and control knob 162 may be moved relative to each other. Typically, a physician will release the stent 110 by pulling the control handle 168 in the proximal direction toward the control knob 162 while maintaining the control knob 162 in a fixed position. As a result, the retention sheath 120 is withdrawn in the proximal direction. Because the proximal end 112 of the stent 110 abuts the stop 140 on the inner catheter 130, the stent 110 does not move proximally with the retention sheath 120. Instead, the stent 110 remains generally at its predeployment position adjacent the stop 140 of the inner catheter 130. As the retention sheath 120 is withdrawn, the stent 110 is released and expands in a radially outward direction.

One problem that may be experienced with the above-described stent 110 and delivery system 100 is difficulty in precisely releasing the stent 110 at a desired treatment site. Typically, a stent 110 is provided with radiopaque markers or other positional locators that allow the physician to determine the location of the stent 110 while the stent 110 is within the patient's body and housed within the delivery system. A physician will normally use these positional locators to position the stent 110 at the desired treatment site before the stent 110 is released from the delivery system. Thus, it is desirable for the stent 110 to expand and contact the vessel wall 3 (see FIGS. 3-4) at substantially the same longitudinal position at which it is located prior to release. However, in some cases, the stent 110 may move a small distance relative to the inner catheter 130 during release of the stent 110. As a result, the stent 110 may not be deployed precisely where the physician desires to release the stent 110.

Movement of the stent 110 relative to the proximal end 104 of the delivery system may occur during deployment for various reasons. For example, as the control handle 168 is moved proximally toward the control knob 162, friction between the stent 110 and the retention sheath 120 may cause the retention sheath to resist movement relative to the stent 110. The longer the stent, the more difficult it is to move the stent 110 relative to the retention sheath 120. Due to the frictional force between the stent 110 and the retention sheath 120, a portion of the retention sheath withdrawal force provided at the control handle 168 may be transferred from the retention sheath 120 to the stop 140 through the stent 110. This transferred force acts to compress the stop 140 and/or the attached inner catheter 130 in the proximal direction, thereby causing the inner catheter 130 to absorb energy in a spring-like manner. As the withdrawal force overcomes the frictional force, the retention sheath 120 is withdrawn and the stent is released from the retention sheath 120. Upon release of the stent 110, the energy stored in the inner catheter is suddenly released, which may cause the stent 110 to "jump" slightly in the distal direction. This problem may be exacerbated in delivery systems for drug coated stents because the drug coating typically increases the stent's coefficient of friction, thereby resulting in increased inner catheter compression and energy storage. These problems may make it difficult for a physician to precisely deploy a stent 110 at a desired treatment site.

In some cases, with certain stent designs, a stent 110 may be resheathed if the stent 110 is not released at the desired treatment site. For example, if a physician determines that the position of a stent 110 should be changed, the physician may attempt to push the retention sheath 120 distally to recompress the stent 110 into the delivery system. However, this option is of limited usefulness for several reasons. In general, resheathing of a stent 110 must be done before the stent 110 is fully released from the retention sheath 120. Thus, the physician must make this determination when the distal end 114 of the stent 110 has been released but before the proximal end 112 of the stent 110 has been released. After the proximal end 112 of the stent 110 has been released, it is usually difficult or impossible to resheath a stent 110 or change the position of the stent 110. In general, resheathing of a stent 110 only works with stents 110 that have a moderately high longitudinal stiffness. Further, stents 110 that are more longitudinally flexible can be more difficult to resheath.

If a physician does not precisely implant the stent 110 at the desired treatment site, the therapeutic effect of the stent 110 may be reduced. In the event the stent is not accurately deployed at the treatment site, the physician may decide to implant a second stent in order to treat the entire treatment site. In this situation, the physician will usually overlap the ends of the first and second stents to ensure complete coverage along the treatment site. However, overlapped stents may cause other problems related to the potential interference between the two stents, such as increased neointimal hyperplasia.

Generally speaking, there are two basic types of self expanding stents: open cell and closed cell. An example of a closed cell stent is a stent made out of braid, such as the one depicted in the attached Figures. This type stent works like a "finger trap" sleeve so that the harder the two ends are pulled away from each other, the tighter is the stent becomes. Closed cell stents are typically retrievable and shorten in length as they are expanded (i.e. they experience "foreshortening" during expansion). In operation, a distal end of the braid of the closed cell stent is anchored to the vessel and the proximal end of the stent is pushed distally to increase the diameter of the stent. In contrast, an open cell stent, for example and without limitation, the Zilver® stent sold by Cook Medical, Inc. of Bloomington, Ind., is typically not retrievable and experiences substantially no foreshortening during expansion.

An improved delivery system is shown in FIGS. 2(a)-(e). As shown in FIG. 2(a), the external appearance of the delivery system 200 is similar to the delivery system 100. The delivery system 200 may include a retention sheath 220 having a proximal end 224 and a distal end 222, a self-expanding stent 210 having a proximal end 212 and a distal end 214, an inner catheter 230, a plurality of separate rings 270, and a control device 260. The inner catheter may include a guidewire lumen 255 and a distal tip 250 having a proximal surface 252 and a distal end 254. The control device 260 may include a control knob 262, a hollow shaft 263, a locking tab 264, a slot 265, a control handle 268, and a port 269. It should be noted that the inner catheter 230 does not include an integrated stop for the self-expanding stent 210.

The distal tip 250 is attached to a distal end of the inner catheter 230. The inner catheter 230 may be made from a polymer, such as polyamide or the like. Preferably, the distal tip is a separate component that is bonded to the inner catheter 230 with an adhesive. However, it should be understood that the distal tip 250 may be formed as an integral part of the inner catheter 230. The guidewire lumen 255 extends through the center of the inner catheter 230 in an axial direction from the distal tip 250 to the proximal end of the inner catheter 230. A proximal portion of the inner catheter is disposed within a lumen extending through the center of the control handle 268, the shaft 263, and the control knob 262. A proximal end of the inner catheter 230 is fixedly attached to the control knob 262.

The control handle 268 is disposed around the shaft 263 and is slideably movable relative to the shaft 263 in a proximal-distal direction from an initial position, in which the distal end of the control knob 262 is spaced axially away from the proximal end of the control handle 268 in an extended configuration, as shown in FIG. 2(a), to a deployment position in which the distal end of the control knob 262 is disposed adjacent the proximal end of the control handle 268, as shown in FIG. 2(c). The proximal end 224 of the retention sheath 220 is connected to the control handle 268 at the distal end 266.

The locking tab 264 may be inserted into the slot 265 and is configured to engage the shaft 263 such that when the locking tab 264 is inserted into the slot 265, the shaft 263 cannot move relative to the control handle 268, thereby preventing inadvertent or premature deployment of the stent 210.

The port 269 may be provided on the control handle to pass fluids, e.g. contrast fluid, through the delivery system to the treatment site. Preferably, the port 269 is in communication with the annular space between the inner catheter 130 and the retention sheath 220, however, it should be understood that the port 269 may be in communication with the guidewire lumen 255 of the inner catheter 230 or a lumen disposed within the retention sheath 220 (not shown).

The retention sheath 220 has an outer diameter and an inner surface that defines an inner lumen extending axially along its length. The retention sheath 220 is disposed around the inner catheter 230 in a co-axial configuration and extends from the proximal end 224, which is attached to the control handle 268, to the distal end 222, which is disposed adjacent to the proximal side 252 of the distal tip 250. The retention sheath 220 may be a composite of different materials, and the base material of the retention sheath 220 preferably is made from a lubricious material, for example PTFE (polytetrafluoroethylene) or the like. The retention sheath 220 also may incorporate wire coils or braids to increase the sheath's resistance to torsional and extension forces.

The plurality of separate rings 270 are disposed in the annular space between the outer surface of the inner catheter 230 and the inner surface of the retention sheath 220. The rings are stacked in a co-axial configuration such that the inner catheter 230 is disposed within a center hole defined by the inner diameter of each ring. In one embodiment, each individual ring has the same outer diameter, the same inner diameter, and the same thickness, as measured in the axial direction. For example, the rings may have an axial thickness ranging between 0.001 inches and 0.05 inches, an outer diameter ranging between 0.025 inches and 0.4 inches, and an inner diameter ranging between 0.02 and 0.395 inches. However, it should be understood that the rings are not limited thereto and may have an axial thickness greater than 0.05 inches in some applications. The rings may also have an inner diameter that is less than 0.02 inches or greater than 0.395 inches. Preferably, the inner diameter of the rings is slightly larger than the outer diameter of the inner catheter 230, and the outer diameter of the rings is slightly smaller than the inner diameter of the retention sheath 220 in order to facilitate placement of the rings in the annular space between the inner catheter 230 and the retention sheath 220 during the assembly process and to avoid restriction of the retention sheath 220 during withdrawal. The rings are preferably made from metal, for example, stainless steel, nitinol, tungsten, or titanium. However, it should be understood that the rings may be made from any substantially incompressible non-metallic material, such as glass, ceramic, or carbon composite. In a preferred embodiment, the rings are made of 304 stainless steel cannula, and have an outer diameter of less than or equal to 0.4 inches, and a radial thickness of 0.005 inches.

As shown in FIGS. 2(d) and (e), the distal end 266 of the control handle 268 includes a threaded portion 267. The proximal end 224 of the retention sheath 220 is flared outward and is secured between a cap 290 and a curved portion of the distal end 266. The cap 290 is threadably attached to the threaded portion 267 of the distal end 266 of the control handle 268. Preferably, a proximal surface of the proximal most ring in the plurality of separate rings 270 abuts a flat reaction surface 201 of the control knob 262. However, it should be understood that the proximal most ring may abut a reaction surface, or be otherwise secured at any point along the control device 260. As shown in FIG. 2(b), a distal surface of the distal most ring in the plurality of separate rings 270 abuts the proximal end 212 of the stent 210, while the remaining rings are disposed between the distal most ring and the proximal most ring. The proximal and distal surfaces of each of the rings disposed between the distal most ring and the proximal most ring abut at least a portion of the proximal or distal surfaces of the adjacent rings.

As shown in FIG. 2(b), the rings may have a square cross-sectional shape. However, it should be understood that the ring shape is not limited thereto and may have various cross-sectional shapes, such as circular, triangular, oval, trapezoidal, octagonal, or any quadrilateral shape.

The stent 210 is disposed at the distal end 222 of the retention sheath 220 in a compressed configuration, such that the stent 210 exerts a radially outward force against the inner surface of the retention sheath 220. The retention sheath 220 restrains the stent 210 in the compressed configuration. Preferably, the inner catheter 230 extends through the center of the stent 210. The distal end 214 of the stent 210 is disposed adjacent to the proximal surface 252 of the distal tip 250. Preferably, the distal tip 250 has an outer diameter that is slightly smaller than the inner diameter of the retention sheath 220, thereby allowing the distal tip 252 to retract into the retention sheath 220. The retention sheath 220 may include a tapered portion at the distal end 222 to provide a smooth transition from the distal tip 252 to the outer diameter of the retention sheath 220. The distal tip 250 may include a tapered portion 251 that tapers from a maximum outer diameter at the proximal surface 252 to a minimum outer diameter at the distal end 254 and extends distally from the proximal surface 252 to the distal end 254. The maximum outer diameter of the distal tip 250 at the proximal end 252 is larger than the outer diameter of the stent 210 in the compressed configuration, but smaller than the inner diameter of the stent 210 in the uncompressed, or deployed configuration. In another embodiment, the maximum outer diameter of the distal tip 250 is substantially the same diameter as the outer diameter of the retention sheath 220, thereby providing a smooth transition between the distal end 222 of the retention sheath 220 and the distal tip 250.

The improved stent delivery system 200 may be assembled by compressing the stent 210 and inserting the stent 210 in a compressed configuration into the inner lumen of the retention sheath 220 at the distal end 222. As the stent 210 is inserted into the sheath, the stent exerts a radially outward force against the retention sheath 220. Once the stent 210 is positioned within the retention sheath 220, the stent 210 expands radially outward until the outer surface of the stent 210 contacts the inner surface of the retention sheath 220. The proximal end of the inner catheter 230 is then inserted into the inner lumen of the distal end 222 of the retention sheath 220 through the center of the compressed stent 210. The inner catheter 230 is fed axially in a proximal direction through the length of the retention sheath 220 until the proximal surface 252 of the distal tip 250 abuts the distal end 214 of the compressed stent 210. Of course it should be understood that the inner catheter 230 may be initially formed with an integral distal tip 250, or the distal tip 250 may be a separate component that is attached to a distal end of the inner catheter 230 prior to insertion into the retention sheath 220.

A plurality of separate and individual rings 270 are placed around a mandrel or wire, preferably by inserting a leading end of the mandrel through the center hole of the rings. The leading end of the mandrel or wire may then be inserted into the proximal end of the inner catheter 230 disposed within the retention sheath 220. The rings 270 may then be transferred from the mandrel into the annular space between the outer surface of the inner catheter 230 and the inner surface of the retention sheath 220 by applying a force against the rings in the distal direction, or by gravity. Once all of the rings have been inserted into the annular space between the inner catheter 230 and the retention sheath 220, the inner catheter 230 and the retention sheath 220 are attached to the control device 260.

In operation, initially, the guidewire 2 is advanced through a trocar into a desired vessel or cavity using the Seldinger technique which is conventional and well known in the art. The guidewire is then advanced through the patient's vasculature or cavity until it reaches the desired treatment site. Once the guidewire 2 is in the desired position, a proximal end of the guidewire 2 is inserted into the distal end of the guidewire lumen 255. The delivery system 200 is then inserted into a patient's vasculature or cavity by sliding the delivery system 200 along the guidewire 2 in a distal direction. Because the plurality of separate rings 270 are not connected, the individual rings are able to move slightly relative to each other, thus allowing the co-axial assembly of rings to flex and bend with the retention sheath 220 and inner catheter 230 as the delivery system 200 is guided through the patient's vasculature. However, the individual rings 270 are preferably spaced tightly enough between the proximal end 212 of the stent 210 and the reaction surface on the control device 260 that at least a portion of each individual ring abuts the adjacent rings, even in areas where the catheter is bent or curved, as shown in FIG. 3(b). As the delivery system 200 is moved in a distal direction, it is guided through the patient's vasculature by the guidewire 2 to a treatment site, for example, a stenosis. The stent 210 may be positioned at the treatment site using radiopaque markers located on the stent 210. The radiopaque markers allow a physician to visualize the stent 210 from outside the patient's body using x-ray fluoroscopy.

Figure 3A:
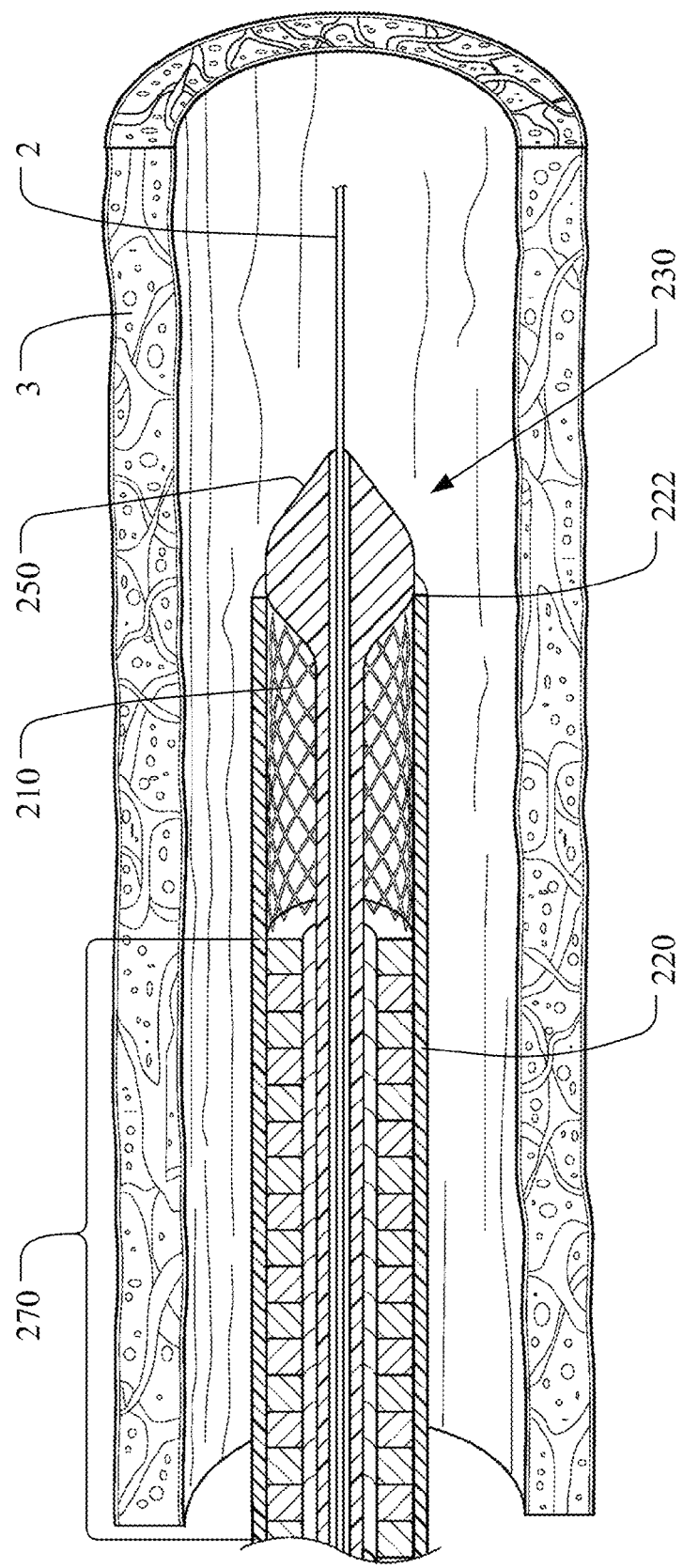
FIG. 3(a) is a partial side cross-sectional view of the delivery system in an undeployed state and positioned in a body passageway.
Figure 3B:
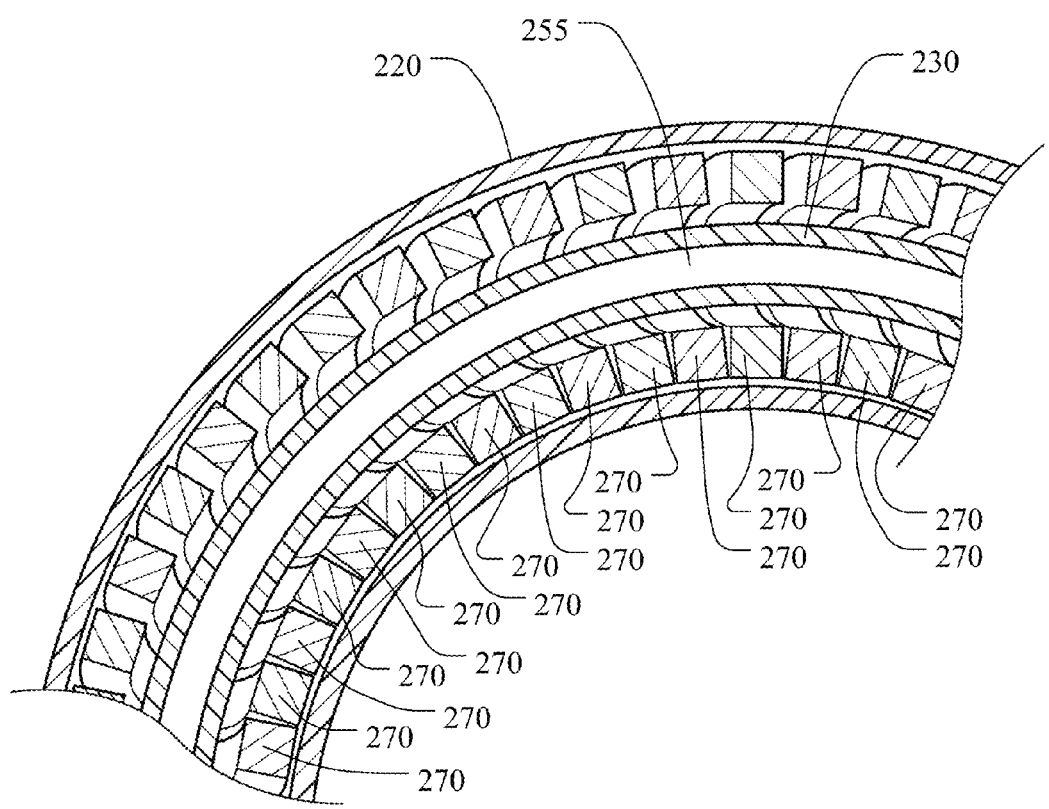
FIG. 3(b) is a cross-sectional view of an intermediate portion of the delivery system of FIG. 3(a) in a curved configuration.
Figure 4:
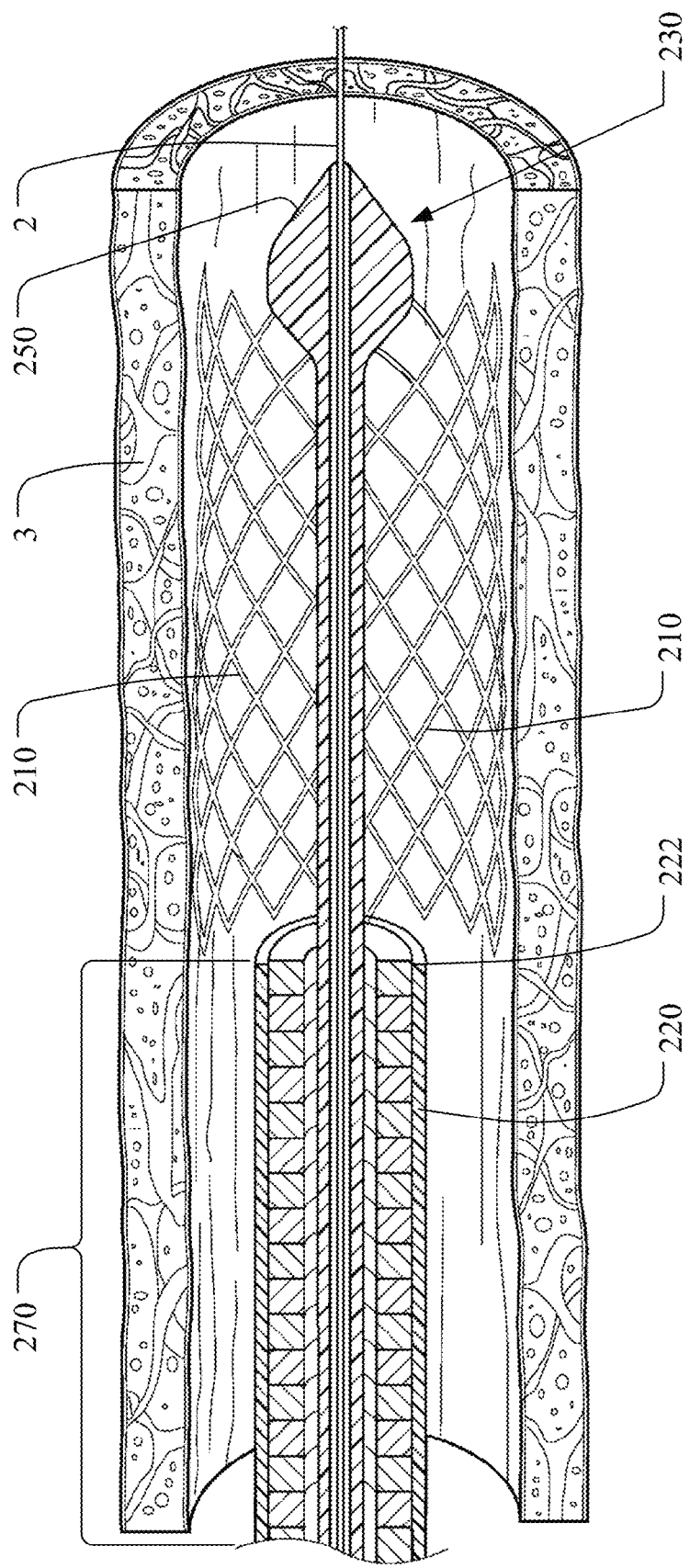
FIG. 4 is a partial side cross-sectional view of the delivery system of FIG. 3 in a deployed state.

As illustrated in FIGS. 3(a) and 4, once the stent 210 is in position at the treatment site, the physician pulls the control handle 260 toward the control knob 262, which causes the retention sheath 220 to move in the proximal direction relative to the inner catheter 230. Due to frictional forces caused by the outward radial force of the compressed stent 210 against the inner surface of the retention sheath 220, a portion of the retraction force applied at the control handle 268 is transferred to the stent 210, thereby forcing the proximal end 212 of the stent 210 against the distal most ring of the plurality of separate rings 270 disposed adjacent the proximal end 212 of the stent 210.

Because each of the individual rings in the plurality of separate rings 270 abuts at least a portion of the rings adjacent thereto, the plurality of separate rings 270 forms a continuous and substantially incompressible assembly extending from the proximal end 212 of the stent 210 to the reaction surface 201 of the control device 260. Thus, as the retention sheath 220 is retracted in the proximal direction, the plurality of separate rings 270 provides a reaction surface for the stent 210 that is anchored at the control device 268, thereby preventing the stent 210 from moving in an axial direction toward the control handle 268. Furthermore, because the plurality of separate rings 270 is substantially incompressible, energy from the retraction force introduced at the control device 268 is not stored in the inner catheter 230 or the plurality of separate rings 270, thereby avoiding the spring effect of a conventional inner catheter, which causes the stent to jump when deployed.

When the distal end 222 of the retention sheath 220 is retracted over the stent 210 the stent 210 progressively expands until the retention sheath 220 is completely removed from the outer surface of the stent 210. At this point, as shown in FIG. 4, the stent 210 is completely released from the delivery system 200, and the stent 210 expands radially outwardly against the vessel wall 3 of the treatment site.

Additionally, because the proximal surface 252 of the distal tip 250 abuts the distal end 214 of the stent 210 and the distal most ring in the plurality of separate rings 270 abuts the proximal end 212 of the stent 210, the gap 180 of conventional delivery systems is eliminated, and any associated delay and inaccuracy in deployment of the stent 210 is avoided.

In an alternative embodiment, one or more of the rings in the plurality of separate rings 270 may be made from, or coated with, a radiopaque material, for example, heavy metals such as gold, platinum or tungsten. In one embodiment, the distal most ring, which is disposed adjacent to the proximal end 212 of the stent 210, is radiopaque, thereby giving the physician an additional marker indicating the position of the stent 210 relative to the treatment site. Alternatively, the ring disposed adjacent to the distal most ring in the proximal direction may be radiopaque in order to aid the physician in distinguishing between the distal end of the plurality of separate rings 270 and the proximal end 212 of the stent 210. In this embodiment the distal most ring may be made from a non-metallic material, which is not readily visible using x-ray fluoroscopy, to further aid the physician in distinguishing the proximal end 212 of the stent from the plurality of separate rings 270.

In another embodiment, two rings spaced apart at a predetermined distance may be radiopaque. In this configuration the two radiopaque rings in the stack of rings 270 allow the delivery system 200 to also act as a sizing catheter, as is known in the art. It should be understood that the two radiopaque rings may be placed anywhere along the length of the delivery system 200 between the proximal end of the stent 210 and the control device 260, however, it is preferable that the two radiopaque rings are disposed in a position along the length of the delivery system 200 that is likely to be inserted into a relatively straight portion of the vasculature to allow for more accurate sizing.

Figure 5A:
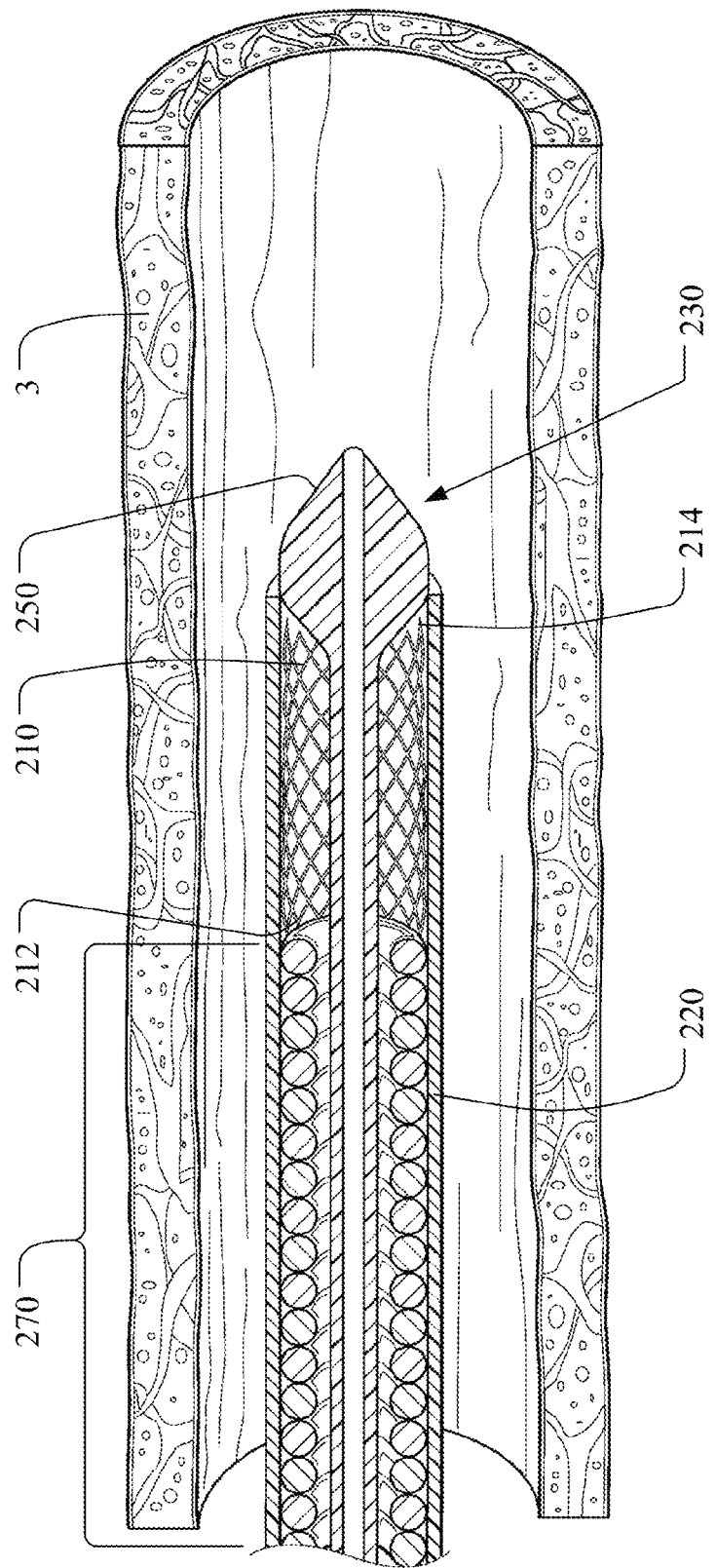
FIG. 5(a) is a partial side cross-sectional view of an alternative embodiment of the implantable self-expanding medical device delivery system of FIG. 3 in an undeployed state.
Figure 5B:
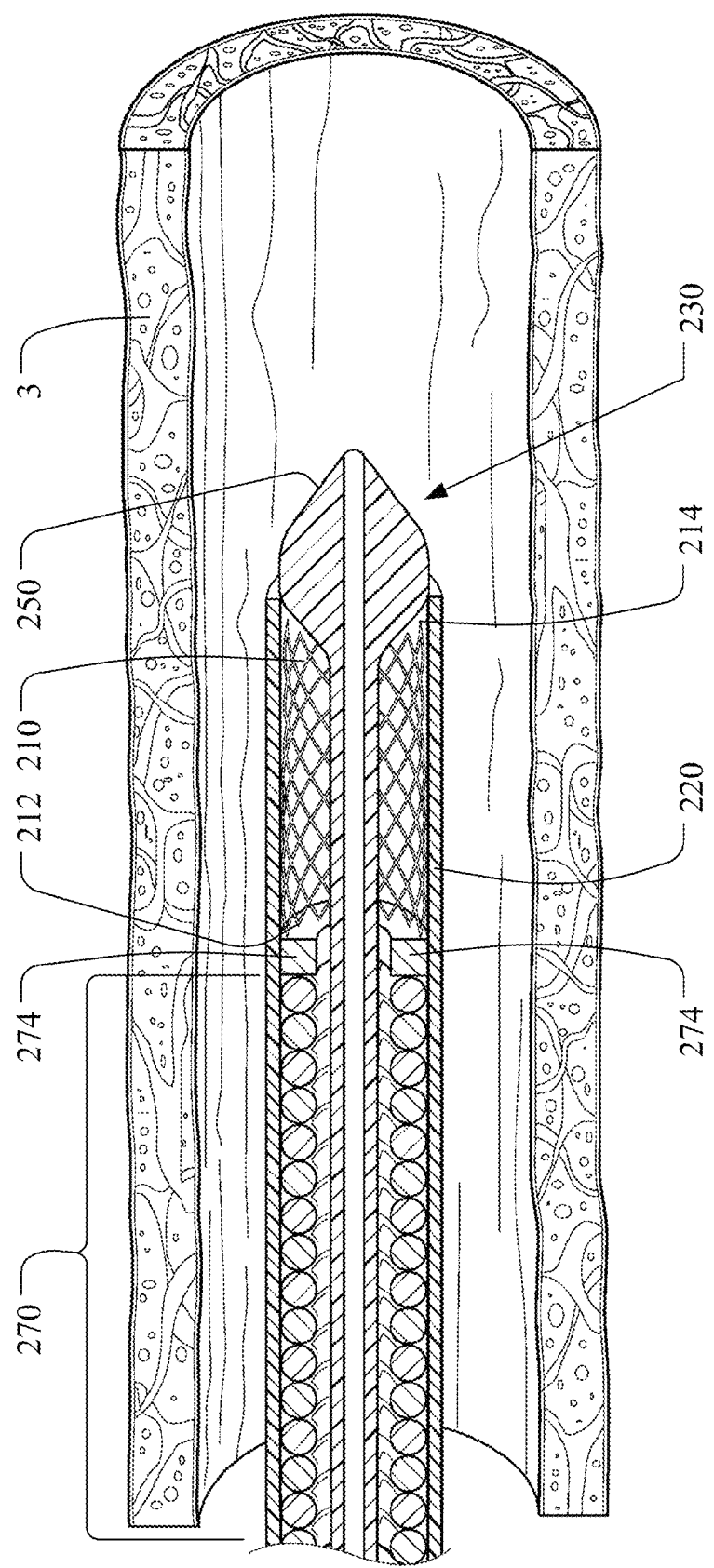
FIG. 5(b) is a partial side cross-sectional view of another alternative embodiment of the implantable self-expanding medical device delivery system of FIG. 3 in an undeployed state.

FIGS. 5(a) and (b) illustrate another embodiment of the delivery system 200, in which the rings of the plurality of separate rings 270 have a round cross-sectional shape. In FIG. 5(b), all of the rings in the plurality of separate rings 270 have a round cross-sectional shape with the exception of the distal most ring 274, which has a square cross-sectional shape to provide a more stable reaction surface for the proximal end 212 of the stent 210, and to prevent the proximal end 212 of the stent 210 from becoming wedged in a spaced formed between the rounded surface of a ring having a round cross-section and the inner surface of the retention sheath 220.

The plurality of separate rings 270 in this configuration function in the same manner as the plurality of separate rings 270 having a square cross-sectional shape described above. However, the round cross-sectional shape of the rings reduces the contact area between the individual rings, thereby increasing the flexibility of the delivery system.

Figures 6A, 6B:
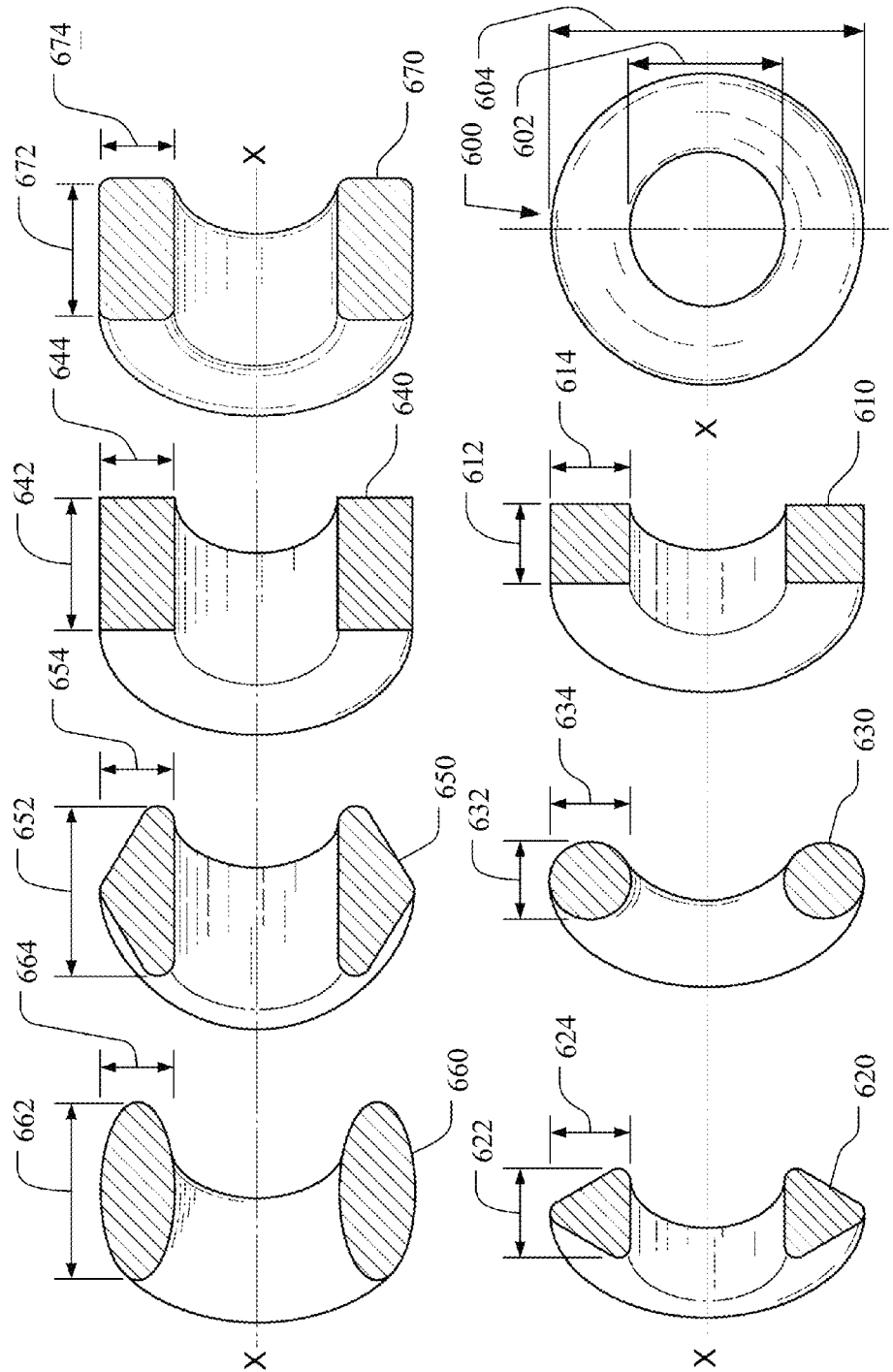
FIG. 6(a) is a top view of a single ring.
FIG. 6(b) illustrates perspective cross-sectional views of exemplary cross-sectional shapes of the ring of FIG. 6(a)

FIGS. 6(a) and (b) illustrate detailed views of the individual rings in the plurality of separate rings 270. FIG. 6(a) illustrates a top view of a ring having any of the cross-sectional shapes depicted in FIG. 6(b). Each ring 600 has a circular shape with an inner diameter 602 and an outer diameter 604. FIG. 6(b) illustrates a number of alternative cross sectional shapes for the rings in the plurality of separate rings 270: a square cross-section 610 having a radial thickness 614 and an axial thickness 612; a triangular cross-section 620 having a radial thickness 624 and an axial thickness 622; a round cross-section 630 having a radial thickness 634 and an axial thickness 632, a rectangular cross-section 640 having a radial thickness 644 and an axial thickness 642; an elongated triangular cross-section 650 having a radial thickness 654 and an axial thickness 652; an oval cross-section 660 having a radial thickness 664 and an axial thickness 662; and a substantially rectangular cross-section with rounded corners 670, the substantially rectangular cross-section 670 having a radial thickness 674 and an axial thickness 672. The axial thicknesses 612, 622, 632, 642, 652, 662, and 672 are measured along a central axis x-x of the rings 610, 620, 630, 640, 650, 660, and 670. In one embodiment, all the rings in the plurality of separate rings have the same cross-sectional shape, as well as the same radial and axial thicknesses. However, it should be understood that in other embodiments individual rings 270 may have different cross sectional shapes, and/or different radial or axial thicknesses in order to adjust the flexibility of the portion of the delivery system 200 housing the plurality of separate rings 270. For example and without limitation, the axial thickness may vary between 0.001 and 0.05 inches, and the radial thickness may vary between 0.001 and 0.005 inches.

FIGS. 7(a)-(c) illustrate another embodiment of the delivery system 700 in which the axial thickness of the individual rings in the plurality of separate rings 270 increases in the proximal direction. FIG. 7(a) illustrates the distal end of the delivery system 700. As shown in FIG. 7(a), the delivery system 700 includes a plurality of separate rings 770, with each ring having an axial thickness 772 as measured along a central axis x-x.

FIG. 7(b) illustrates an intermediate portion of the delivery system 700 disposed between the distal end shown in FIG. 7(a) and a control device 260. As shown in FIG. 7(b), the delivery system 700 includes a plurality of separate rings 770 with the rings disposed toward the distal end having the same axial thickness 772 as the rings depicted in FIG. 7(a). However, rings located toward the proximal end of the intermediate portion have an axial thickness 774, which is greater than the axial thickness 772.

FIG. 7(c) illustrates a proximal portion of the delivery system 700 disposed adjacent to the control device 260. As shown in FIG. 7(c), the delivery system 700 includes a plurality of rings 770 in which rings disposed near the distal end of the proximal portion of the delivery system 700 have an axial thickness 774, while rings disposed in an intermediate portion of the proximal portion of the delivery system 700 have a different axial thickness 776, and rings located toward the proximal end of the proximal portion of the delivery system 700 have a different axial thickness 778. Preferably, the axial thickness 774 is less than the axial thickness 776, which is less than the axial thickness 778. For example, the axial thickness 772 may be 0.001 inches, the axial thickness 774 may be 0.002 inches, the axial thickness 776 may be 0.003 inches, and the axial thickness 778 may be 0.005 inches.

In operation, portions of the delivery system 200 having a smaller axial thickness, such as the distal end shown in FIG. 7(a) result in a greater number of rings over a given distance as compared to the intermediate portion shown in 7(b) and the proximal portion shown in 7(c). Because the delivery system 700 relies on the movement of individual rings relative to one another to provide the flexibility necessary to navigate through tortuous vasculature, areas having a higher number of rings over a given area are more flexible than areas having a lower number of rings in that same area. In other words, the flexibility of the delivery system 700 is inversely proportional to the axial thickness of the individual rings. Consequently, the delivery system 700 progressively decreases in flexibility from the distal end to the control device 260. However, it should be understood that the rings are not limited to the configuration depicted in FIG. 7, and rings having different thicknesses may be disposed at different locations along the length of the delivery system 200 as necessary in order to tune the desired flexibility of the delivery system 200.

Although the majority of the preceding detailed description has been made with reference to self-expanding stents, it should be understood that the delivery system of the present invention is not limited thereto, and may be used for any number of implantable medical devices, including for example and without limitation, occluding devices, balloon expanding stents, coils, valves, or filters. Furthermore, it should also be understood that in one embodiment, the plurality of separate rings 270 may be a continuous helical coil extending from the reaction surface 201 of the control handle 268 to the proximal end of the stent 212 or other implantable medical device.

While preferred embodiments of the invention have been described, it should be understood that the invention is not so limited, and modifications may be made without departing from the invention. The scope of the invention is defined by the appended claims, and all devices that come within the meaning of the claims, either literally or by equivalence, are intended to be embraced therein. Furthermore, the advantages described above are not necessarily the only advantages of the invention, and it is not necessarily expected that all of the described advantages will be achieved with every embodiment of the invention.

I claim:

1. A delivery system for an implantable medical device, comprising:
   a retention sheath comprising a proximal end, a distal end, and an inner lumen extending from said proximal end to said distal end, wherein said retention sheath is movable in an axial direction from a pre-deployment position to a deployment position;
   an implantable medical device disposed within said inner lumen of said retention sheath, said retention sheath thereby restraining said implantable medical device;
   a plurality of separate rings disposed within said inner lumen of said retention sheath in a stacked co-axial configuration, wherein each ring in said plurality of separate rings abuts at least a portion of an adjacent ring;
   an inner catheter comprising an outer surface having a diameter that is less than an inner diameter of said plurality of separate rings and a distal tip having an outer diameter that is greater than said inner diameter of said plurality of separate rings, wherein said distal tip is disposed at a distal end of said inner catheter, and said inner catheter is disposed within a space defined by said inner diameter of said plurality of separate rings; and
   a control device configured to be located outside of a patient's body and operated by a physician to control deployment of said implantable medical device by moving said retention sheath axially relative to said plurality of separate rings,
   wherein said plurality of separate rings extends to a reaction surface in said control device and is substantially non-compressible in said axial direction and a longitudinal length of said plurality of separate rings in said stacked co-axial configuration does not change when said retention sheath is moved from said pre-deployment position to said deployment position.

2. The delivery system according to claim 1, wherein said implantable medical device is a self-expanding stent.

3. The delivery system according to claim 1, wherein said plurality of separate rings extends from said proximal end of said retention sheath in said pre-deployment position to a proximal end of said implantable medical device.

4. The delivery system according to claim 1, wherein each of said plurality of separate rings has a cross-sectional shape selected from one of the group consisting of quadrilateral, circular, elliptical, and triangular.

5. The delivery system according to claim 1, wherein at least one ring in said plurality of separate rings is radiopaque.

6. The delivery system according to claim 1, wherein said plurality of separate rings is made of a metal selected from one of the group consisting of nitinol, stainless steel, and titanium.

7. The delivery system according to claim 1, wherein said implantable medical device is a self-expanding stent, and said plurality of separate rings extends from said proximal end of said retention sheath in said pre-deployment position to a proximal end of said implantable medical device.

8. The delivery system according to claim 7, wherein each of said plurality of separate rings has a cross-sectional shape selected from one of the group consisting of quadrilateral, circular, elliptical, and triangular.

9. The delivery system according to claim 8, wherein said plurality of separate rings is made of a metal selected from one of the group consisting of nitinol, stainless steel, and titanium.

10. The delivery system according to claim 9, wherein at least one ring in said plurality of separate rings is radiopaque.

11. A delivery system for an implantable medical device, comprising:
  a retention sheath comprising a proximal end, a distal end, and an inner lumen extending from said proximal end to said distal end, wherein said retention sheath is movable in an axial direction from a pre-deployment position to a deployment position;
  an implantable medical device disposed within said inner lumen of said retention sheath, said retention sheath thereby restraining said implantable medical device;
  a plurality of separate rings disposed within said inner lumen of said retention sheath in a stacked co-axial configuration, wherein each of said rings in said plurality of separate rings abuts at least a portion of an adjacent ring;
  an inner catheter comprising an outer surface having a diameter that is less than an inner diameter of said plurality of separate rings and a distal tip having an outer diameter that is greater than said inner diameter of said plurality of separate rings, wherein said distal tip is disposed at a distal end of said inner catheter, and said inner catheter is disposed within a space defined by said inner diameter of said plurality of separate rings; and
  a control device configured to be located outside of a patient's body and operated by a physician to control deployment of said implantable medical device by moving said retention sheath axially relative to said plurality of separate rings, wherein said plurality of separate rings extends to a reaction surface in said control device,
  wherein each ring in said plurality of separate rings has a thickness in an axial direction, and said thickness varies among at least some rings in said plurality of separate rings.

12. The delivery system according to claim 11, wherein the implantable medical device is a self-expanding stent.

13. The delivery system according to claim 11, wherein said plurality of separate rings extends from said proximal end of said retention sheath in said pre-deployment position to a proximal end of said implantable medical device.

14. The delivery system according to claim 11, wherein said plurality of separate rings are stacked in a continuous co-axial configuration extending from said proximal end of said retention sheath in said pre-deployment position to said proximal end of said self-expanding stent.

15. The delivery system according to claim 11, wherein said thickness of said individual rings in said plurality of separate rings increases in an axial direction toward said proximal end of said retention sheath.

16. The delivery system according to claim 11, wherein each of said plurality of separate rings has a cross-sectional shape selected from one of the group consisting of quadrilateral, circular, elliptical, and triangular.

17. The delivery system according to claim 11, wherein at least one ring in said plurality of separate rings is radiopaque.

18. The delivery system according claim 11, wherein said plurality of separate rings is made from a metal selected from one of the group consisting of nitinol, stainless steel, and titanium.

19. The delivery system according to claim 11, wherein the implantable medical device is a self-expanding stent, said thickness of said individual rings in said plurality of separate rings increases in an axial direction toward said proximal end of said retention sheath, and said plurality of separate rings is made from a metal selected from one of the group consisting of nitinol, stainless steel, and titanium.

20. The delivery system according to claim 11, wherein said plurality of separate rings are stacked in a continuous co-axial configuration extending from said proximal end of said retention sheath in said pre-deployment position to said proximal end of said self-expanding stent, and each of said plurality of separate rings has a cross-sectional shape selected from one of the group consisting of quadrilateral, circular, elliptical, and triangular.

* * * * *

UNITED STATES PATENT AND TRADEMARK OFFICE
CERTIFICATE OF CORRECTION

| | | |
|---|---|---|
| PATENT NO. | : 8,992,591 B2 | Page 1 of 1 |
| APPLICATION NO. | : 12/435689 | |
| DATED | : March 31, 2015 | |
| INVENTOR(S) | : Fred T. Parker | |

It is certified that error appears in the above-identified patent and that said Letters Patent is hereby corrected as shown below:

<u>In the Claims</u>

In Column 16, Line 35, after "according", please insert -- to --.

Signed and Sealed this
Fourteenth Day of July, 2015

Michelle K. Lee
*Director of the United States Patent and Trademark Office*